(12) United States Patent
Jungnickel et al.

(10) Patent No.: US 8,661,596 B2
(45) Date of Patent: Mar. 4, 2014

(54) DRIVE DEVICE FOR DRIVING A BRUSH ELEMENT OF AN ELECTRIC TOOTHBRUSH

(75) Inventors: Uwe Jungnickel, Königstein/Tauns (DE); Benedikt Heil, Ober-Mörlen (DE); Christian Neyer, Eschborn (DE); Bernhard Kraus, Braunfels (DE)

(73) Assignee: Braun GmbH, Kronberg (DE)

( * ) Notice: Subject to any disclaimer, the term of this patent is extended or adjusted under 35 U.S.C. 154(b) by 715 days.

(21) Appl. No.: 12/519,483

(22) PCT Filed: Dec. 1, 2007

(86) PCT No.: PCT/EP2007/010443
§ 371 (c)(1),
(2), (4) Date: Jun. 16, 2009

(87) PCT Pub. No.: WO2008/077454
PCT Pub. Date: Jul. 3, 2008

(65) Prior Publication Data
US 2010/0132139 A1     Jun. 3, 2010

(30) Foreign Application Priority Data
Dec. 23, 2006 (DE) .................... 10 2006 061 381

(51) Int. Cl.
*A46B 13/02* (2006.01)
*A61C 17/22* (2006.01)

(52) U.S. Cl.
USPC ............. 15/22.1; 15/22.2; 15/22.4; 310/50; 310/80; 310/81

(58) Field of Classification Search
USPC ............................................ 15/22.1, 230.16
IPC ....................................................... A46B 13/00
See application file for complete search history.

(56) References Cited

U.S. PATENT DOCUMENTS

| 3,676,218 | A | 7/1972 | Sawyer |
| 5,189,751 | A | 3/1993 | Giuliani et al. |

(Continued)

FOREIGN PATENT DOCUMENTS

| DE | 103 55 446 | 6/2005 |
| DE | 10355446 A1 | 6/2005 |

(Continued)

OTHER PUBLICATIONS

International Search Report for PCT/EP2007/010443, May 14, 2008.

*Primary Examiner* — Monica Carter
*Assistant Examiner* — Stephanie Berry
(74) *Attorney, Agent, or Firm* — John P. Colbert; Vladimir Vitenberg

(57) ABSTRACT

A toothbrush drive includes a first drive component for generating a magnetic field and a second drive component driven in both a translational and rotational manner under the influence of the magnetic field. A transmission element is deflected out of a predetermined position for transmission of both translational and rotary movement of the second drive component. The deflection of the transmission element varies along its longitudinal axis. A transmission element can be deflected out of a predefined position for transmission of a translatory movement and a rotational movement of the second drive component to the brush element along a longitudinal axis of the transmission element. The deflection of the transmission element out of the predefined position is varied along the longitudinal axis of the transmission element.

28 Claims, 15 Drawing Sheets

(56) References Cited

U.S. PATENT DOCUMENTS

2002/0163701 A1* 11/2002 Plesko .......................... 359/199
2006/0255665 A1* 11/2006 Kraus et al. .................... 310/36

FOREIGN PATENT DOCUMENTS

| EP | 1193844 A1 | 3/2002 |
| EP | 1 193 844 | 4/2002 |

* cited by examiner

DRIVE DEVICE FOR DRIVING A BRUSH ELEMENT OF AN ELECTRIC TOOTHBRUSH

BACKGROUND

The invention relates to a drive device for driving a brush element of an electric toothbrush. In addition, the invention relates to an electric toothbrush having such a drive device and to a method for operating such a drive device.

Various toothbrush head motive means have been proposed, providing, in general a limited range or fixed combination of linear or rotational oscillation or vibration. Accordingly, improvements are sought in driving the brush element of an electric toothbrush.

SUMMARY

The details of one or more embodiments of the invention are set forth in the accompanying drawings and the description below. Other features, objects, and advantages of the invention will be apparent from the description and drawings, and from the claims.

One aspect of the invention features a toothbrush drive including a first drive component for generating a magnetic field and a second drive component driven in both a translational and rotational manner under the influence of the magnetic field. A transmission element is deflected out of a predetermined position for transmission of both translational and rotary movement of the second drive component. The deflection of the transmission element varies along its longitudinal axis.

Another aspect of the invention features a drive device for driving a brush element of an electric toothbrush including a first drive component for generating a magnetic field and a second drive component, which can be driven both translationally and rotationally by the influence or action of the magnetic field. In addition, the drive device has a transmission element, which can be deflected out of a predefined position for transmission of a translatory movement and a rotational movement of the second drive component to the brush element along a longitudinal axis of the transmission element. It is advantageous in some cases that the deflection of the transmission element out of the predefined position is varied along the longitudinal axis of the transmission element such that the deflection of the transmission element does not consistently have the same value over the entire longitudinal axis of the transmission element. Instead there are positions along the longitudinal axis where the deflection of the transmission element assumes different values.

Another aspect of the invention features a drive device for driving a brush element of an electric toothbrush. The drive device includes a first drive component for generating a magnetic field; and a second drive component which can be driven to both translatory movement and rotational movement by the influence of the magnetic field. The drive device further includes a transmission element which can be deflected out of a predefined position for transmission of a translatory movement and a rotational movement of the second drive component to the brush element along a longitudinal axis of the transmission element; and wherein the deflection of the transmission element out of the predefined position varies along the longitudinal axis of the transmission element.

In some cases, the predefined position of the transmission element corresponds to an equilibrium position, which the transmission element assumes without the action of the magnetic field on the second drive component. In some cases, the equilibrium position is arranged outside of a position of the transmission element in which the action of the magnetic field on the second drive component has a maximum value.

In some implementations, at least one axial position of the transmission element executes primarily a rotational movement in the transmission of the translatory movement and the rotational movement to the second drive component.

In some implementations a component of the deflection of the transmission element oriented across the longitudinal axis of the transmission element out of the predefined position along the longitudinal axis of the transmission element varies linearly.

In some implementations the deflection of the transmission element out of the predefined position has a first direction within a first range along the longitudinal axis of the transmission element and has a second direction opposite the first direction within a second range along the longitudinal axis of the transmission element at the same time.

In some implementations the transmission element is excitable to a translatory vibration and to a rotational vibration. In some cases, the translatory vibration and the rotational vibration have different resonant frequencies. In some cases, the transmission element can be excited to a pendulum vibration about a pendulum axis running across the longitudinal axis of the transmission element.

In some cases, the transmission element can be excited to a bending vibration across the longitudinal axis of the transmission element. In some cases the transmission element can selectively be excited to the pendulum vibration or to the bending vibration.

In some implementations at least one suspension is provided to support the transmission element. In some cases different suspensions are provided for the rotational and the translatory vibration of the transmission element. In some cases the suspension is arranged in one of the area of the pendulum axis of the transmission element, the area of a vibration node of the transmission element, and the area of an axial end of the transmission element. In some cases at least one suspension comprises an elastic element.

In a particular implementation the transmission element (4) comprises a coupling area for coupling the brush element and the ratio of the vibration amplitudes can be varied between the translatory vibration and the rotational vibration of the transmission element in the coupling area of the transmission element.

In some cases the coupling area predefines through its shape the orientation of the brush element relative to the transmission element, so that bristles arranged on the brush element form an acute angle with the deflection direction of the translational vibration of the transmission element.

In some implementations, the transmission element is rigidly connected to the second drive component in a rotationally fixed manner.

In some implementations the second drive component is arranged axially next to the first drive component.

In some implementations the first drive component comprises a coil.

In some implementations the first drive component comprises a pole shoe arrangement with an internal pole shoe element and an external pole shoe element surrounding the internal pole shoe element radially.

In some cases the second drive component comprises a permanent magnet.

In a particular implementation the first drive component and the second drive component are arranged inside a housing comprising a ferromagnetic material.

Another aspect of the invention features a drive device for driving a brush element of an electric toothbrush, wherein the drive device includes a first drive component for generating a magnetic field; and a second drive component which can be driven to both translatory and rotational movement by the action of the magnetic field. The drive device further includes a transmission element that can be deflected out of a predefined position for transmission of a translatory movement and a rotational movement of the second drive component to the brush element along a longitudinal axis of the transmission element; and wherein the transmission element is attached to a suspension between two freely movable axial ends of the transmission element.

Features of the drive device advantageously allow a rotational movement and a translatory movement to be generated with comparatively little effort and transmitted to the brush element. It is especially advantageous that the drive device is designed as a direct drive and generates the rotational and translatory movement directly through the influence or action of the magnetic field on the second drive component. Thus, this configuration avoids the conventional gears used to generate a translatory movement from a rotational movement or, conversely, a rotational movement from a translatory movement.

Additional efficiencies are provided in that roller bearings or friction bearings are not necessary for supporting the moving components of the drive device, and a wide range of movement patterns can be generated with the drive device, such that minor design changes must be made in the drive device at any rate. Furthermore, it is advantageous that minimal unwanted vibrations are generated by the drive device.

In a particular implementation, the predefined position of the transmission element corresponds to an equilibrium position assumed by the transmission element without the influence of the magnetic field on the second drive component. The drive device may be constructed so that the action of the magnetic field on the second drive component has a maximum value in the equilibrium position. A force acting externally, which may occur due to the pressure of the brush element in toothbrushing, for example, would then result in a displacement in the transmission element and thus a reduction in the drive force of the drive device. However, in other implementations the equilibrium position can be arranged outside of a position of the transmission element in which the action of the magnetic field on the second drive component is at a maximum value. Such an implementation of the drive device has the advantage that the driving force of the drive device first increases with an increase in the contact pressure of the brush element, thereby preventing a collapse of the movement of the brush element with an increase in the contact pressure.

In a particular implementation of the drive device, at least one axial position of the transmission element in the transmission of the translatory and rotational movement of the second drive component executes only a rotational movement. Thus, the transmission of unwanted vibrations can be minimized by suspension of the transmission element in such an axial position.

In a particular implementation, a component of the deflection of the transmission element out of the predefined position along the longitudinal axis of the transmission element is varied linearly or depending on a nonlinear function, said component being oriented across the longitudinal axis of the transmission element. It is likewise possible that the deflection of the transmission element out of the predefined position has a first direction within the first range along the longitudinal axis of the transmission element and at the same time has a second direction opposite the first direction within a second range along the longitudinal axis of the transmission element.

In a particular implementation, the transmission element can be excited to a translatory vibration and to a rotational vibration. This makes it possible to achieve a high efficiency of the drive device. The translatory and rotational vibration can have different resonant frequencies allowing selective excitation of the translatory and rotational vibration. In particular the transmission element can be excited to a pendulum vibration about a pendulum axis running across the longitudinal axis of the transmission element. Relatively large deflections can be achieved in this way, and it is easily possible to implement a desired step-down or step-up ratio for transmission of the movement of the second drive component to the brush element through the choice of the axial position of the pendulum axis. It is also possible for the transmission element to be excitable to a bending vibration across the longitudinal axis of the transmission element. Relatively high vibration frequencies can thus be achieved with a comparatively low drive force. Furthermore, desired step-up or step-down ratios can be predefined via the adjustment in stiffness of the transmission element including the brush element. Another advantage is that the vibrating masses can be equalized within the transmission element to minimize unwanted vibrations. Additional benefits may be provided by a configuration in which the transmission element is optionally excitable to the pendulum vibration or to bending vibration. This allows selection between different movement patterns and thus allows individual adaptation of a preferred or selected movement pattern by the user of the electric toothbrush.

In some implementations, the drive device has at least one suspension for supporting the transmission element, allowing rotational and/or translatory vibration of the transmission element. Different suspensions are preferably provided for the rotational and translatory vibration of the transmission element. Thus, the suspensions can be coordinated with the respective vibrating movements and the load per suspension is low. In a particular implementation of the drive device, the suspension is arranged in the area of the pendulum axis of the transmission element or in the area of a vibration node of the transmission element. The load on the suspension is the lowest there, and at any rate unwanted vibrations transmitted via the suspension are minimized. In addition, the suspension can be arranged in the area of an axial end of the transmission element. It is especially advantageous if at least one suspension is designed as or has an elastic element. Such a suspension is inexpensive to implement and resists wear. Furthermore, the friction can be minimized. Another advantage is that such a suspension may also be used as a restoring element for the vibrating movement of the transmission element. In particular, the suspensions may be designed as or may have elastic elements. In this case, the cost of roller bearings or friction bearings to support the transmission element can be eliminated.

The transmission element may have a coupling area for connecting the brush element. It is advantageous if the ratio of the vibration amplitudes between the translatory vibration and the rotational vibration of the transmission element is variable in the coupling area of the transmission element. This allows individual adjustment of a desired movement pattern by the user of the electric toothbrush. In a particular implementation of the drive device, the coupling area predetermines through its shape the orientation of the brush element relative to the transmission element, so that bristles arranged on the brush element form an acute angle with the direction of deflection of the translatory vibration of the transmission element. In this way, a good cleaning effect can be achieved with the electric toothbrush.

In some implementations, the transmission element is connected to the second drive component in a rotationally fixed manner. The transmission element is rigidly connected to the second drive component to provide reliable transmission of the movement of the second drive component to the transmission element. In some cases, the transmission element can be designed as a shaft, for example.

In a particular implementation of the drive device, the second drive component is arranged axially next to the first drive component. This has the advantage that the translatory movement of the second drive component in the radial direction is not impaired by the first drive component. In a particular implementation, the first drive component includes a coil and a cable line supplying electric power to the coil. In addition, the first drive component can have a pole shoe arrangement with an internal pole shoe element and an external pole shoe element, which surrounds the internal pole shoe element radially. Thus, a desired field distribution of the magnetic field may be generated by the first drive component to produce desired movements. In particular implementations, the second drive component has at least one permanent magnet. Thus, a cable connection or electrical supply the second drive component is not required.

In a particular implementation, the first drive component and the second drive component are arranged inside a housing made of a ferromagnetic material to shield against stray magnetic fields.

Another aspect of the invention features a drive device for driving a brush element of an electric toothbrush, with a first drive component for generating a magnetic field, a second drive component which can be driven to both translatory movement and rotational movement by the action of the magnetic field and with a transmission element that can be deflected out of a predefined position for transmission of a translatory movement and a rotational movement of the second drive component to the brush element along a longitudinal axis of the transmission element. The transmission element is attached to a suspension between its two axial ends.

Fastening of the transmission element between its two axial ends can be easily accomplished and allows efficient transmission of the driving movement from the second drive component to the brush element. It is also advantageous if the axial ends of the transmission element are freely movable. The suspension may be designed as or may have an elastic element. Furthermore, an essentially rotational plate spring arrangement may be provided for generating a rotational vibration.

Another aspect of the invention features a drive device for driving a brush element of an electric toothbrush, having a first drive component for generating a magnetic field and a second drive component which has a magnetic arrangement with several permanent magnets or magnetizable areas arranged axially next to the first drive component. The permanent magnets or magnetized areas are arranged according to a pattern with regard to their dimensions and their magnetic orientation in the magnetic arrangement, said pattern being neither axially symmetrical nor point symmetrical.

This allows for a compact design providing both a translatory movement and a rotational movement by a direct interaction between the first and second drive components. In a particular implementation, the magnetic arrangement has permanent magnets of different sizes or magnetizable regions of different sizes.

Another aspect of the invention features a drive device for driving a brush element of an electric toothbrush, having a first drive component for generating a magnetic field and a second drive component, which has a magnetic arrangement with multiple permanent magnets or magnetized areas arranged axially next to the first drive component. The magnetic arrangement is designed with respect to the dimensions and the magnetic orientation of the permanent magnets or magnetic areas so that when the magnetic field generated by the first drive component is in effect, a force and a torque are exerted on the second drive component.

In particular, the magnetic arrangement may be designed so that a force and a torque are generated when a symmetrical magnetic field is in effect.

Aspects of the invention are useful in an electric toothbrush having one of the drive devices described above for driving the brush element.

Another aspect of the invention features a method of operation of a drive device of an electric toothbrush in which a magnetic field is generated by a first drive component. A second drive component is induced to a translatory movement and rotational movement through the action of the magnetic field. The translatory movement and the rotational movement of the second drive component are transmitted to a brush element by deflection of a transmission element out of a predefined position along a longitudinal axis of the transmission element. The deflection of the transmission element out of the predefined position is varied along the longitudinal axis of the transmission element.

The details of one or more implementations or embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
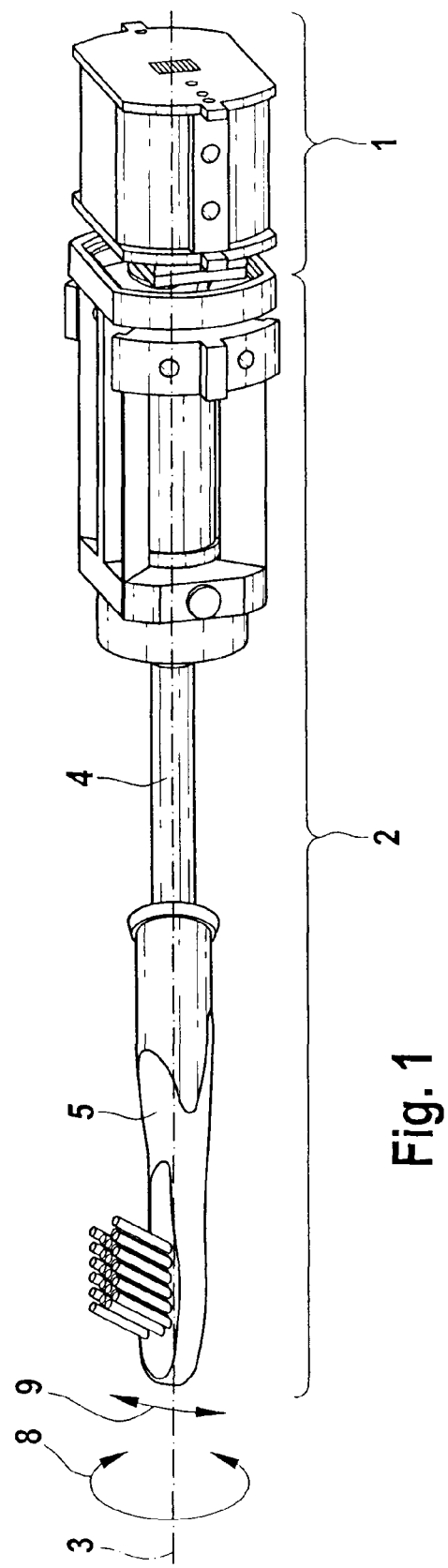
FIG. 1 is a perspective view of one implementation of an electric toothbrush.
Figure 2:
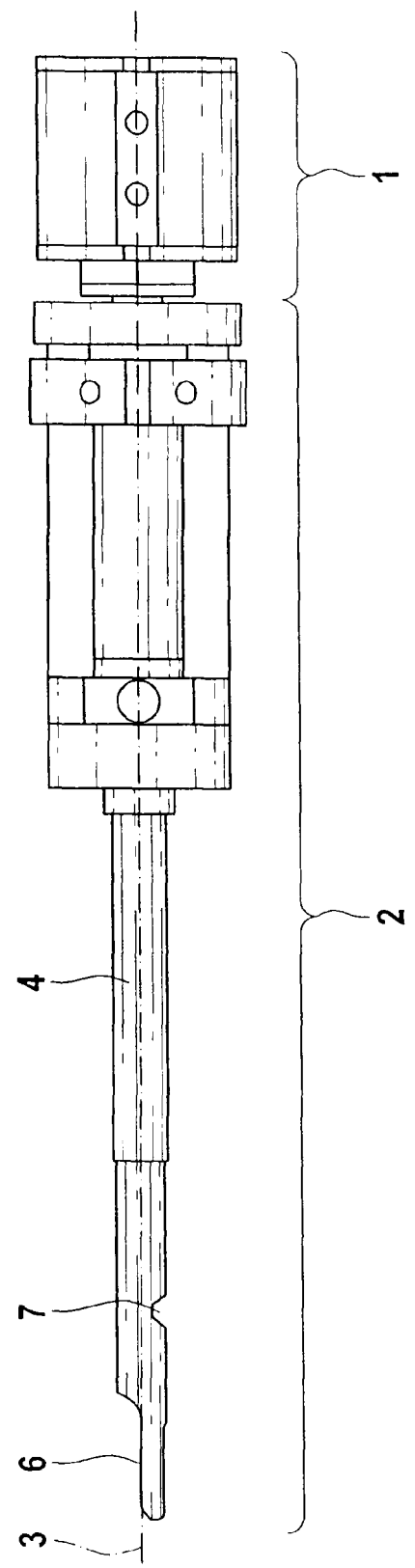
FIG. 2 is a side view of the electric toothbrush of FIG. 1.

FIGS. 1 and 2 show one implementation of an electric toothbrush without the housing to allow a view of the components arranged inside the housing. The electric toothbrush has an electric motor 1 and a vibrating system 2 arranged adjacent to one another axially along a common longitudinal axis 3. The vibrating system 2 has a shaft 4 onto which an attachable brush 5 is attached. The attachable brush 5 is shown in FIG. 1. FIG. 2 shows the electric toothbrush without the attachable brush, so that the area of the shaft 4 holding the attachable brush 5 is visible. Within this area, a flattened area 6 and a recess 7 are formed, serving to secure the attachable brush 5 and the shaft 4 in a rotationally and axially secured manner. The additional components of the vibrating system 2 and the components of the electric motor 1 are described in greater detail below.

The electric motor 1 serves to induce a defined vibrational state in the vibrating system 2. A rotational vibrating movement of the attachable brush 5 can be induced around the longitudinal axis 3 in particular, which is represented by a directional arrow 8, and a translatory vibrating movement of the attachable brush 5 can be induced across the longitudinal axis 3, which is represented by a directional arrow 9.

Figure 3:
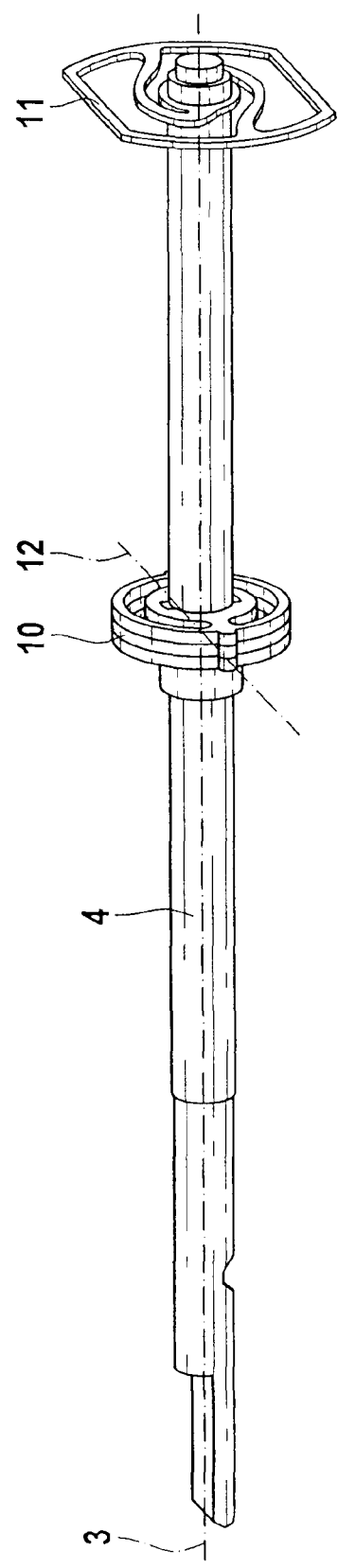
FIG. 3 is a perspective view of one implementation of a bearing of the shaft.

FIG. 3 shows the shaft 4 supported by a first spring 10 and a second spring 11. The first spring 10 is arranged axially between the two ends of the shaft 4 and allows a pendulum movement of the shaft 4 about a pendulum axis 12, which is defined by the first spring 10 and runs across the longitudinal axis 3. This pendulum movement is explained in greater detail with reference to FIG. 4.

The second spring 11 is arranged in the area of the axial end of the shaft 4 opposite the receptacle area for the attachable brush 5 and has a higher stiffness in a direction parallel to the pendulum axis 12 and a lower stiffness in a direction perpendicular to the pendulum axis 12 and to the longitudinal axis 3. The second spring 11 thus acts as an additional guidance of the shaft 4 in a pendulum movement by suppressing movements parallel to the pendulum axis 12 and allowing movements around the pendulum axis 12.

Figure 4:
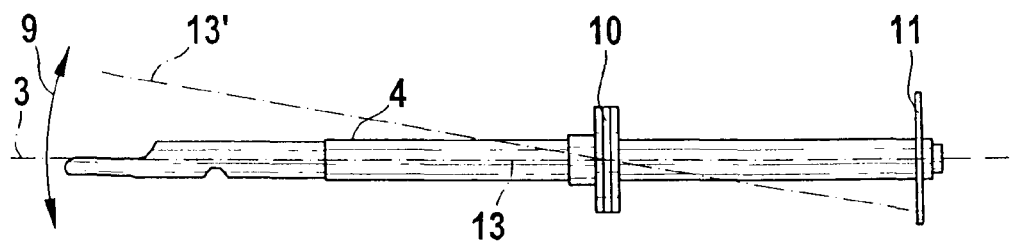
FIG. 4 is a side view of the shaft supported according to FIG. 3 for a first vibrational state.

FIG. 4 shows a side view of the shaft 4, which is mounted according to FIG. 3, for a first vibrational state. The first vibrational state is characterized in that the shaft 4 executes a periodic pendulum movement about the pendulum axis 12. FIG. 4 shows two snapshots of this pendulum movement. A first snapshot is based on a resting or equilibrium state in which the shaft 4 would remain if it were not excited to a vibrating movement. For the equilibrium state, FIG. 4 shows the outlines of the shaft 4 and the two springs 10 and 11. At periodic intervals during the pendulum movement, the shaft 4 assumes a position corresponding to the equilibrium state. The position of the shaft 4 is illustrated by its center line in FIG. 4, where a reference numeral 13 is assigned to the center line in the equilibrium state.

In addition, FIG. 4 shows a deflected state for which the center line of the shaft 4 is shown in FIG. 4 and is labeled with reference numeral 13'. In the deflected state, the shaft 4 is tilted about the pendulum axis 12 in comparison with the equilibrium state, so that the center line 13' of the shaft 4 in the deflected state and the center line 13 of the shaft 4 in the equilibrium state form an angle to one another. This means that the deflection of the shaft 4 out of the resting position is varied along the shaft 4 and there is a deflection toward opposite sides on the two sides of the pendulum axis 12 at the same point in time. The deflection here is understood to be the distance of a point on the shaft 4 in the deflected state from the same point in the resting state. In addition to the dependence of deflection on location, there is also a dependence of deflection on time during the pendulum movement, so that the deflection varies over time for a fixed axial position on the shaft 4. The dependence of the deflection on time and place may also be provided in a different type of movement pattern than the pendulum movement described above and with a different type of design of the toothbrush. The lever effect of the shaft 4 between its end driven by the electric motor 1 on the one hand and its end holding the attachable brush 5 on the other hand can be varied by means of the axial position of the pendulum axis 12 and thus the first spring 10. In other words, the step-down or step-up ratio between the electric motor 1 and the attachable brush 5 can be determined by the axial position of the first spring 10.

Figure 5:
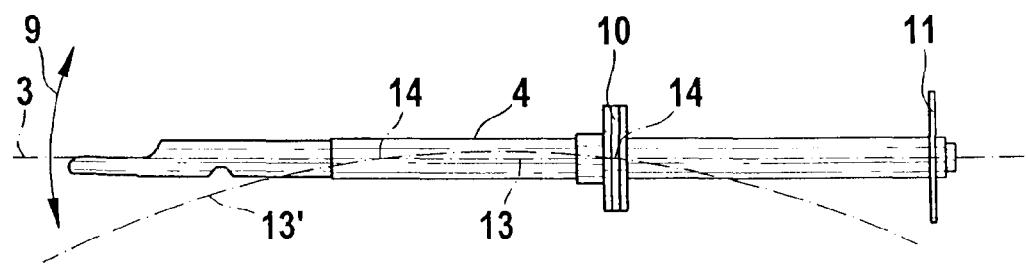
FIG. 5 is a side view of the shaft supported according to FIG. 3 for a second vibrational state.

The pendulum vibration described above constitutes a fundamental vibration of the shaft 4. In addition to this fundamental vibration, higher intrinsic modes may also be excited. The higher intrinsic modes each correspond to a bending vibration in the form of a standing wave 4. FIG. 5 illustrates one example of such a bending vibration.

FIG. 5 shows the shaft 4 supported according to FIG. 3 for a second vibrational state. The second vibrational state is characterized in that the shaft 4 executes a first harmonic in the form of the bending vibration shown. The first harmonic has two vibration nodes 14 in which the shaft 4 remains in its equilibrium position. Outside of the vibration nodes 14, the deflection of the shaft 4 varies over time. In addition, the deflection of the shaft 4 outside of the vibration node 14 varies along the shaft 4 due to the bending at a given point in time.

In a particular implementation the first spring 10 is arranged in the area of one of the vibration nodes 14. As a result, the bending vibration of the shaft 4 is not hindered by the first spring 10 to minimize vibrations transmitted via the first spring 10 to the housing of the electric toothbrush.

The transmission ratio of the movement between the driven end of the shaft 4 and the attachable brush 5 can be influenced via the stiffness of the shaft 4 and of the attachable brush 5. This makes it possible to implement both step-up and step-down ratios.

Figure 6:
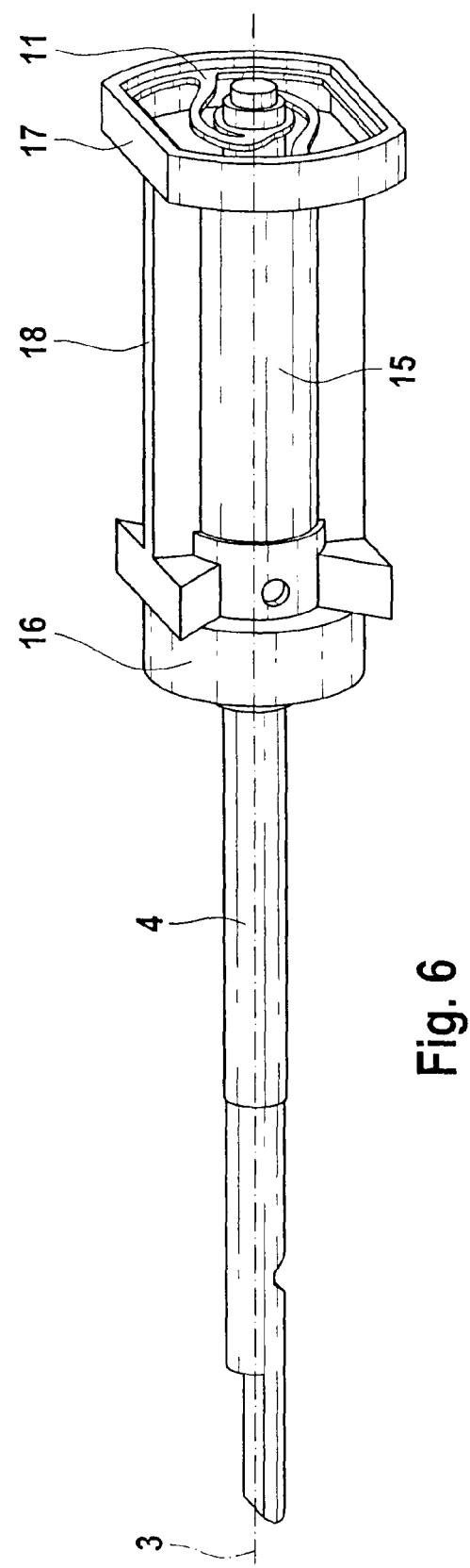
FIG. 6 is a perspective view of a spring carrier configured to receive the first spring and the second spring.

FIG. 6 shows a spring carrier 15 configured to receive the first spring 10 and the second spring 11. The spring carrier 15 receives the first spring 10 in a first receptacle frame 16, the shape of which is coordinated with the first spring 10, and the second spring 11 in a second receptacle frame 17, whose shape is coordinated with the second spring 11. The two receptacle frames 16 and 17 are rigidly connected to one another by means of webs 18 running parallel to the longitudinal axis 3.

Figure 7:
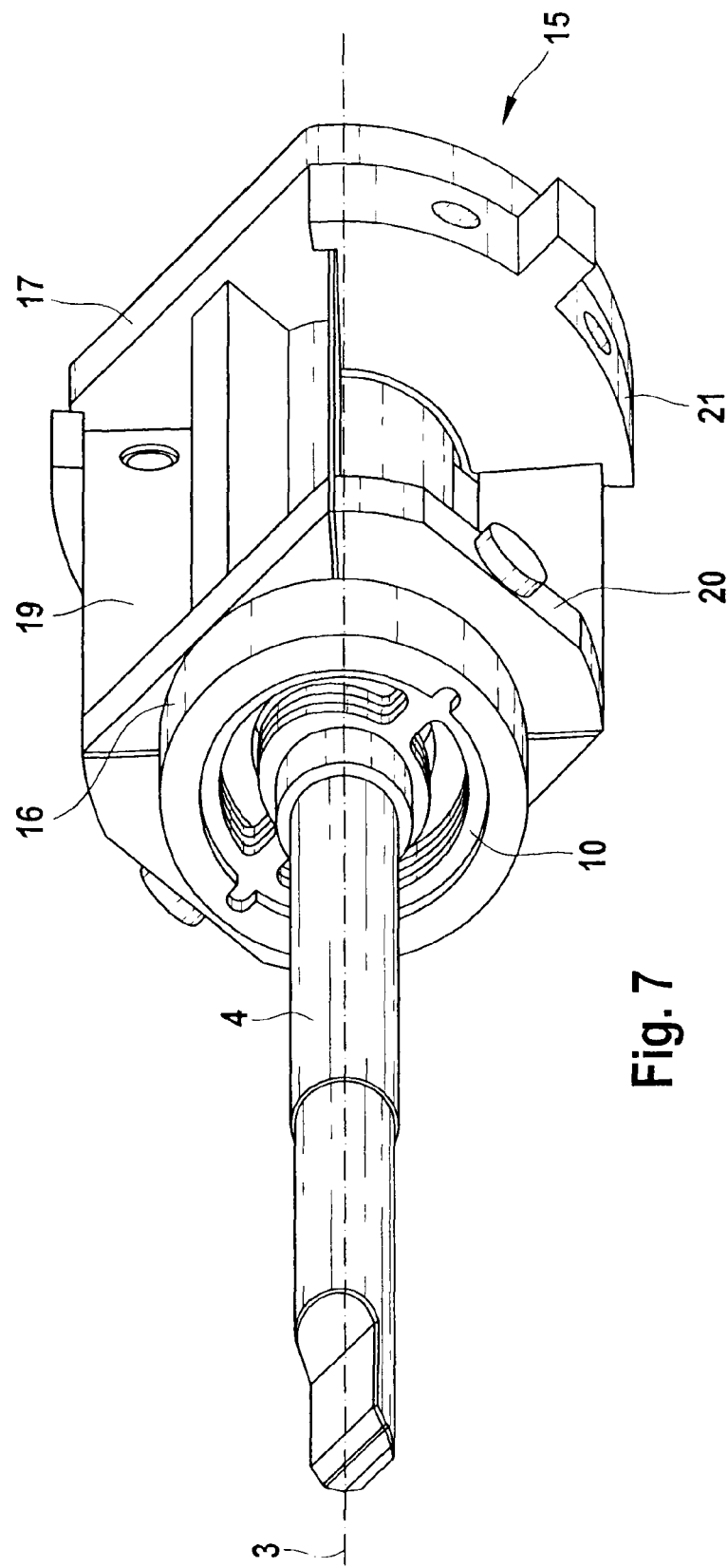
FIG. 7 is a perspective view of an implementation of the vibrating system.

FIG. 7 shows the vibrating system 2 including the spring carrier 15 illustrated in FIG. 6. Four plate springs 19, each designed as a rectangle with one end attached to the spring carrier 15, are mounted in proximity to the first receptacle frame 16 of the spring carrier 15. For example, the plate springs 19 are each clamped at one end between the spring carrier 15 and the clamping piece 20. The longitudinal sides of the plate springs 19 extend in the axial direction based on the shaft 4. The narrow sides of the plate springs 19 extend in the radial direction based on the shaft 4. With their free ends, the plate springs 19 are each attached in pairs to a retaining block 21. Such an arrangement of plate springs 19 suppresses relative movements between the retaining blocks 21 and the spring carrier 15 parallel to the axial direction of the shaft 4 and parallel to the radial direction of the shaft 4. Still, within certain limits, the spring carrier 15 can be rotated relative to the retaining blocks 21.

The implementation of the vibrating system 2 described above thus allows a rotational vibration of the spring carrier 15 including the shaft 4 about the longitudinal axis 3 in relation to the retaining blocks 21 in addition to the pendulum vibration and/or bending vibration of the shaft 4 already explained in detail above. The rotational vibration preferably has a different resonant frequency than the pendulum vibration and/or bending vibration. This makes it possible to stimulate the pendulum vibration and/or bending vibration or the rotational vibration preferentially through the choice of the exciting frequency relative to the resonant frequency. A desired excitation of the pendulum vibration on the one hand or the bending vibration on the other hand may take place via the choice of the excitation frequency if the pendulum vibration and the bending vibration have different resonant frequencies. A combined vibrating movement can be excited through an excitation frequency between the resonant frequencies. It is likewise also possible to induce an excitation having multiple frequency components which are preferably near the respective resonant frequencies and in this way to generate a combined vibrating movement.

Figure 8:
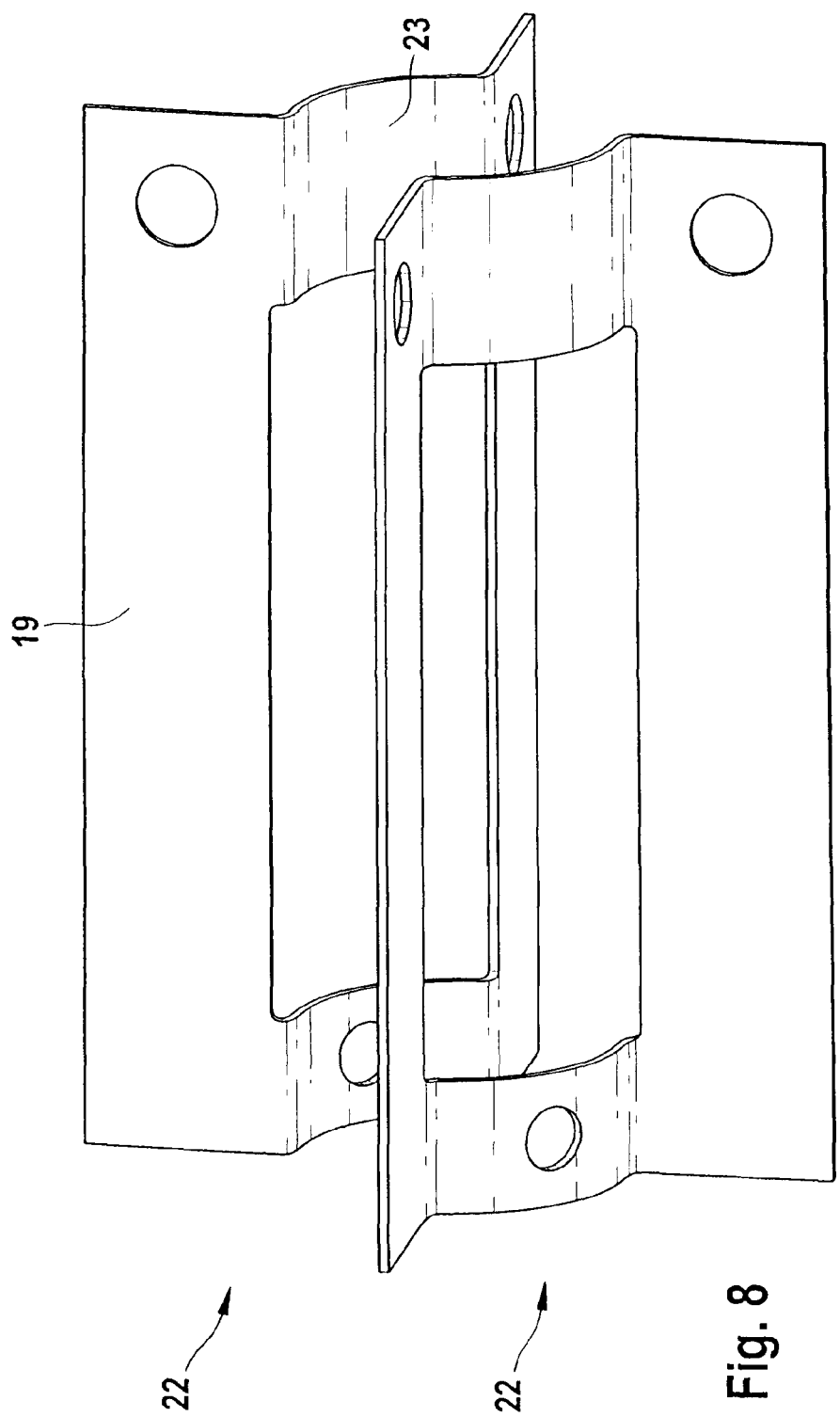
FIG. 8 is a perspective view of one implementation of a set of plate spring modules.

FIG. 8 shows one implementation of a set of plate spring modules 22 used for fixation of the spring carrier 15 on the retaining blocks 21 in a rotationally mobile manner instead of the individual plate springs 19 shown in FIG. 7. Each plate spring module 22 effectively replaces two plate springs 19. The plate spring modules 22 are each embodied as punched/bending parts with two plate springs 19 integrated into each. The two plate springs 19 are joined at their ends by straps 23. The straps 23 can be designed in one piece with the plate springs 19.

Through the use of the plate spring modules 22 instead of the plate springs 19, the number of components to be mounted is reduced. Furthermore, accurate alignment of the plate springs 19 is simplified and the overall installation complexity is reduced.

Figure 9:
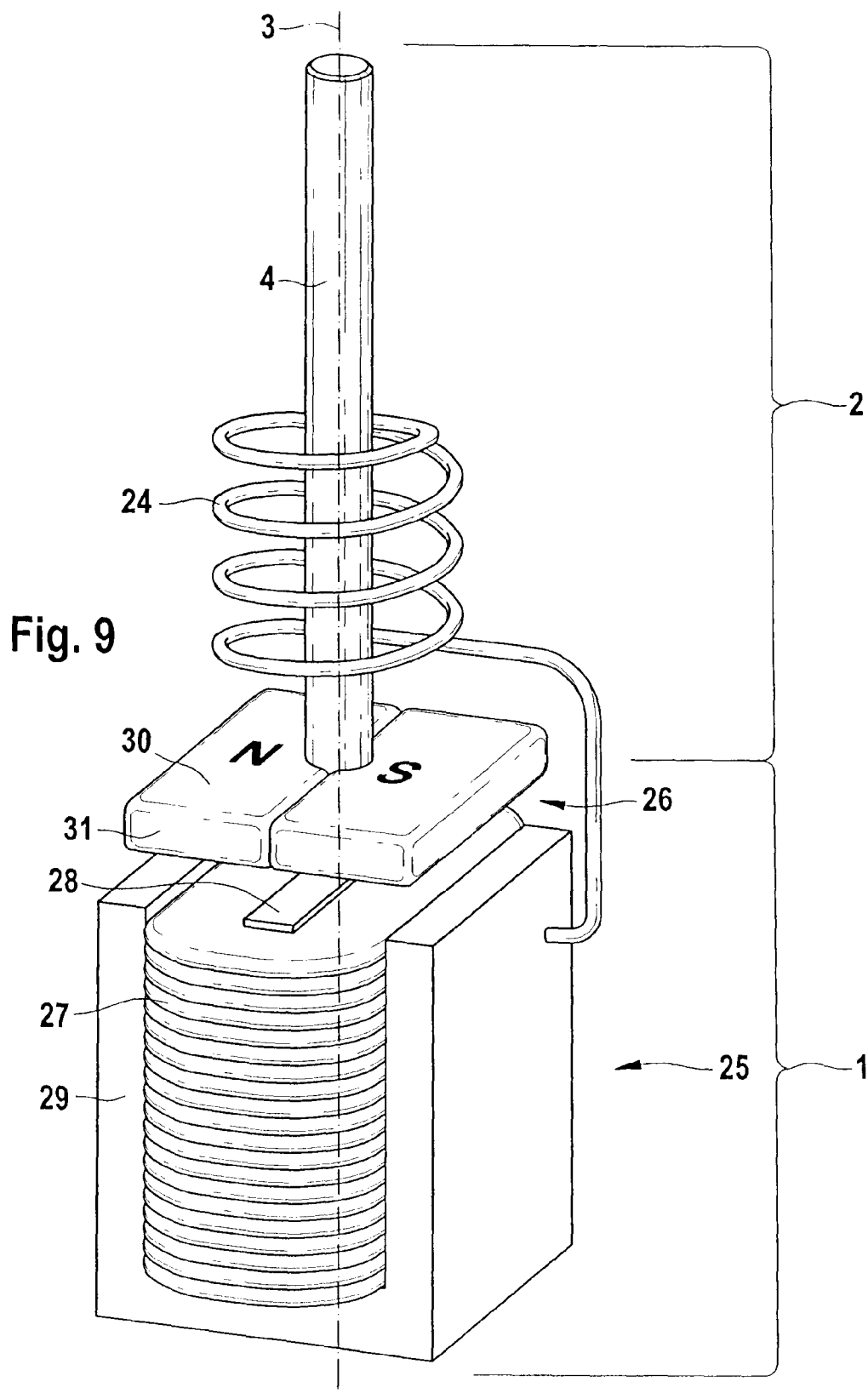
FIG. 9 shows one basic diagram of the electric motor.

FIG. 9 shows a first basic diagram of the electric motor 1. The shaft 4 and a spring element 24 are also shown in FIG. 9, indicating the vibrating system 2. The electric motor 1 has a stator 25 and a rotor 26 arranged axially side by side.

The stator 25 has a coil 27, a coil core 28 and a coil housing 29. The coil 27 is wound around the coil core 28 and arranged inside the coil housing 29. The coil core 28 and the coil housing 29 are both made of ferromagnetic material.

The rotor 26 has a magnetic arrangement 30, which is mechanically connected to the shaft 4. A particular connection is designed to be rigid. In the implementation shown in FIG. 9, the magnetic arrangement 30 has a permanent magnet 31 with the north/south extent running across the longitudinal extent of the coil core 28. Likewise, two permanent magnets 31 can also be provided, with the north/south directions each running parallel to the longitudinal axis 3 and being arranged side by side with an antiparallel polarity. This substitution option also exists with magnetic arrangements 30 having a different design.

When a current flows through the coil 27, a magnetic field is generated, its direction depending on the direction of current in the coil 27. Through the action of the magnetic field on the permanent magnet 31, a magnetic force is generated parallel to the north/south extent of the permanent magnet 31 and the magnetic arrangement 30 is thereby deflected out of its equilibrium position. The spring element 24 generates a restoring force directed toward the equilibrium position. In the equilibrium position, the magnetic arrangement 30 is arranged centrally relative to the coil core 28. By periodic reversal of polarity or at least activation and deactivation of the coil current, for example, at a frequency near the resonant frequency of the vibrating system 2, which also includes the magnetic arrangement 30, the vibrating system 2 is excited to pendulum vibrations or bending vibrations as described above. Rotational vibration is generally not excited absent generated torque.

Figure 10:
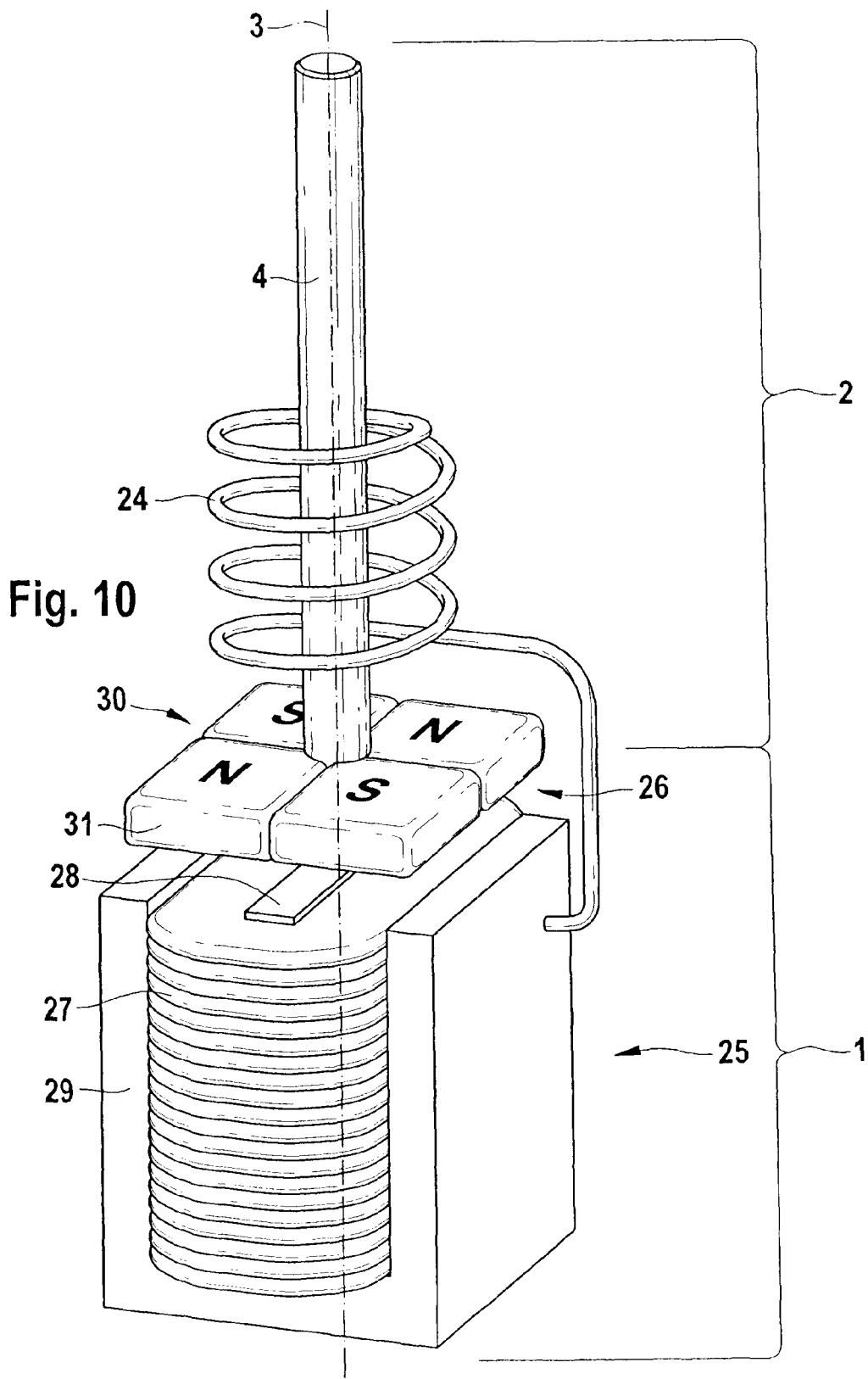
FIG. 10 shows a second diagram of the electric motor.

FIG. 10 shows a second basic diagram of the electric motor 1. The second basic diagram differs from FIG. 9 with regard to the magnetic arrangement 30. Instead of a single permanent magnet 31, the magnetic arrangement 30 has two permanent magnets 31 arranged side by side with an antiparallel polarity. This orientation of the permanent magnets 31 results in a torque being generated by the action of the magnetic field generated by the coil 27 on the magnetic arrangement 30, thereby rotating the magnetic arrangement 30 out of the equilibrium position. In the equilibrium position the north/south extents of the permanent magnets 31 are oriented at a right angle to the longitudinal extent of the coil core 28. The spring element 24 generates a reverse moment directed toward the equilibrium position. Through a periodic change in the magnetic field generated by the coil 27, which can be generated by a corresponding change in the coil current, the vibrating system 2 can be excited to a rotational vibration. Pendulum vibrations or bending vibrations are generally not excited when only torques are generated.

Figure 11:
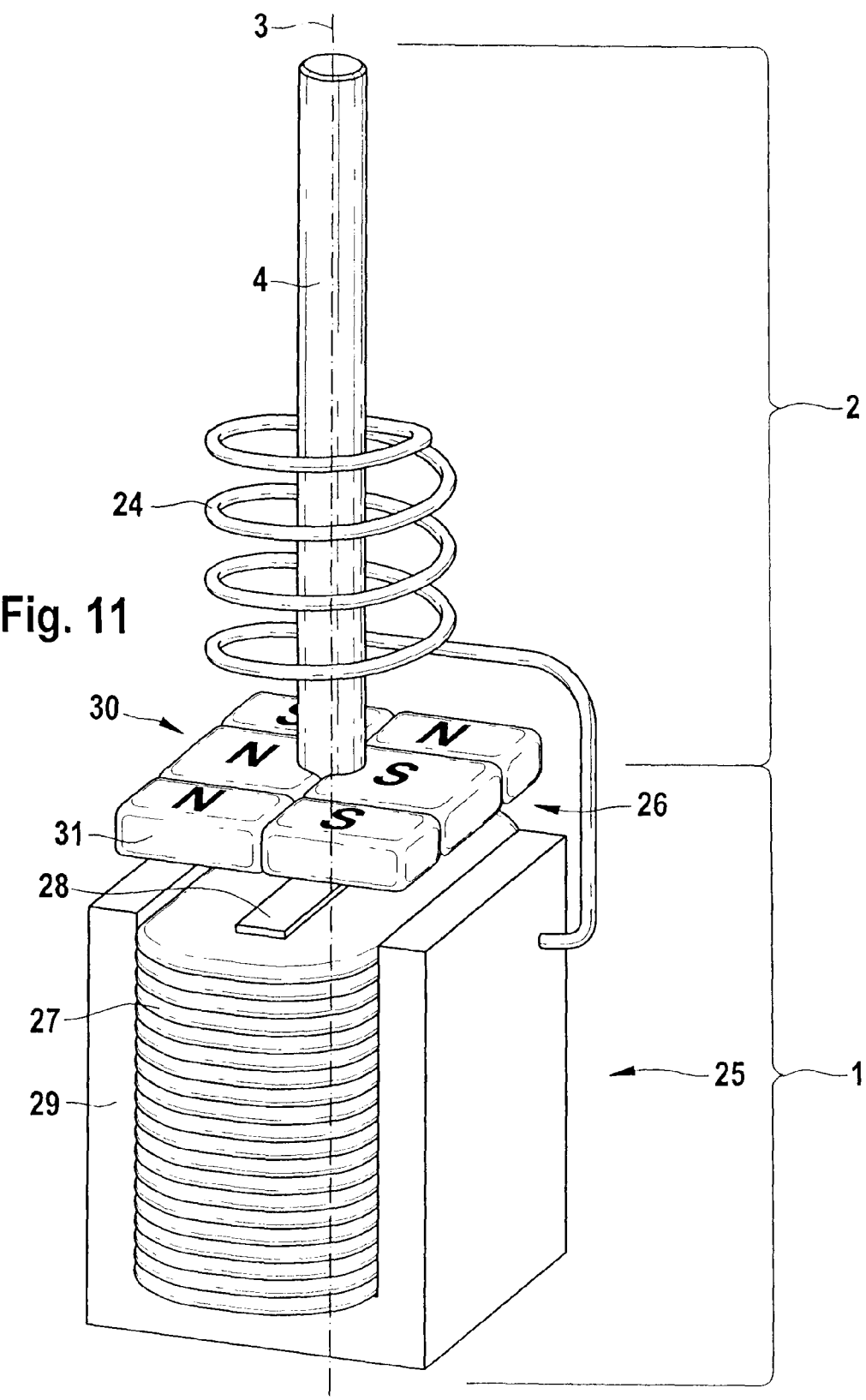
FIG. 11 shows a third basic diagram of the electric motor.

FIG. 11 shows a third basic diagram of the electric motor 1. In the third basic diagram, the rotor 26 has a magnetic arrangement 30, which corresponds to a combination of the magnetic arrangements 30 according to the first and second basic diagrams. The permanent magnet 31 according to the first basic diagram is arranged between the two permanent magnets 31 according to the second basic diagram. The action of the magnetic field generated by the coil 27 on the middle permanent magnet 31 creates a force; the action of the magnetic field generated by the coil 27 on the two external permanent magnets 31 creates a torque. Thus a pendulum vibration and/or a bending vibration as well as a rotational vibration can be excited. There is the possibility of exciting predominately a pendulum vibration, a bending vibration or a rotational vibration in by far the majority of cases through the choice of the excitation frequency relative to the resonant frequency. In a desired amplitude ratio, it is likewise possible to excite a pendulum vibration and/or a bending vibration on the one hand and also to excite a rotational vibration on the other hand. A desired amplitude ratio of different types of vibration can also be achieved by superimposing several excitation frequencies.

The force generated by the action of the magnetic field generated by the coil 27 on the magnetic arrangement 30 is at its maximum when the magnetic arrangement 30 is positioned centrally above the coil core 28, i.e., in the equilibrium position. If the magnetic arrangement 30 is shifted out of the equilibrium position by an external force, then the force created by the action of the magnetic field will decline. The external force may be, in a particular example, the contact pressure to which the attachable brush 5 is exposed when brushing the teeth. There is thus the possibility of deactivating the excitation of the pendulum vibration and/or bending vibration above a predefined contact pressure.

In addition, it is possible to modify the electric motor 1 so that the magnetic arrangement 30 is arranged eccentrically with the coil core 28 in the equilibrium state. In this modification, an increasing contact pressure of the attachable brush 5 initially causes increased excitation of pendulum and/or bending vibrations. The maximum excitation of the pendulum and/or bending vibration occurs when the magnetic arrangement 30 is positioned centrally with respect to the coil core 28 due to the contact pressure. A further increase in contact pressure results in the magnetic arrangement 30 leaving the central position with respect to the coil core 28 and then there is also a reduction in the excitation of the pendulum and/or bending vibration accordingly.

Figure 12:
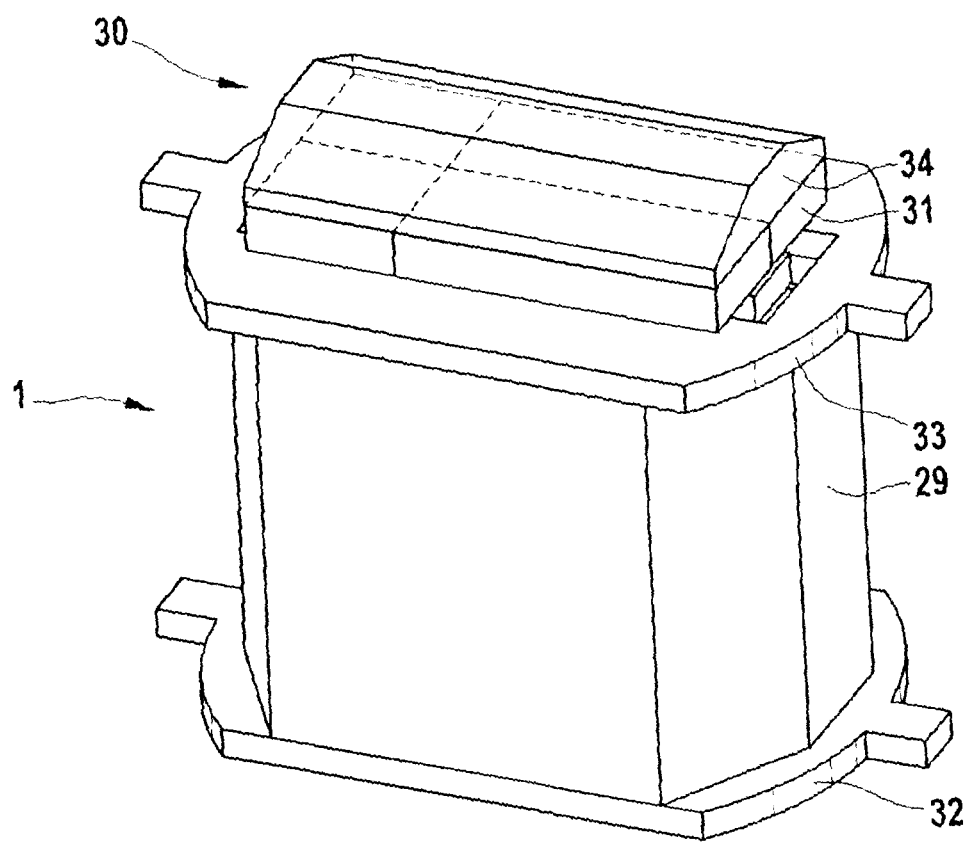
FIG. 12 is a perspective view of one implementation of the electric motor.

FIG. 12 shows an exemplary embodiment of the electric motor 1 in a perspective diagram. In the exemplary embodiment shown here, the coil housing 29 is closed on one axial end with a closing plate 32 made of a ferromagnetic material. A connection between the coil core 28 and the coil housing 29 is formed via the closing plate 32, such that a magnetic flux can be passed over this connection. On the other axial end of the coil housing 29, a pole shoe arrangement 33 is provided over which the magnetic field generated by the coil 27 emerges. The magnetic arrangement 30 is arranged directly next to the pole shoe arrangement 33 axially and has a carrier 34, which can be made of a ferromagnetic material, to receive the permanent magnets 31. The coil housing 29 may also be designed so that it extends beyond the magnetic arrangement 30 to minimize stray magnetic fields.

Figure 13:
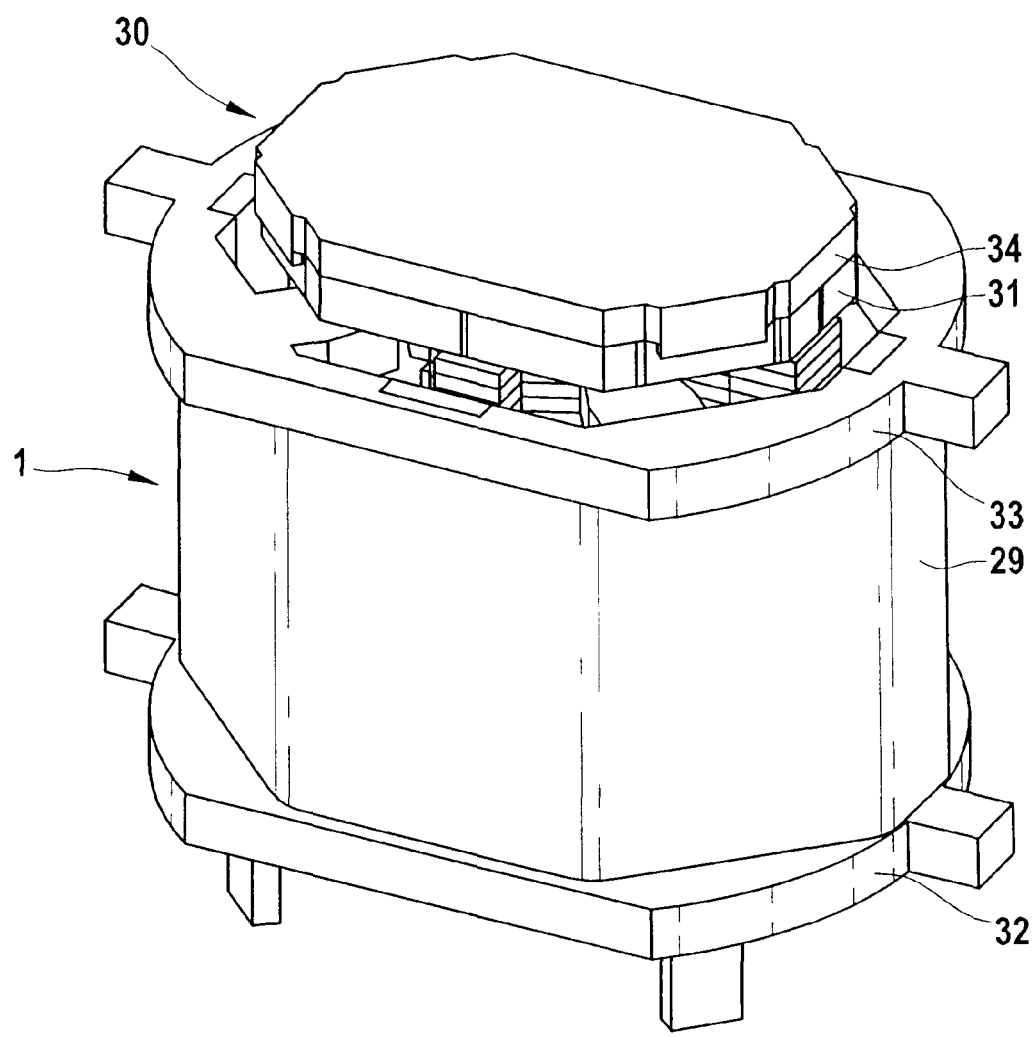
FIG. 13 is a perspective view of another implementation of the electric motor.

FIG. 13 shows another implementation of the electric motor 1 differing from that illustrated in FIG. 12 essentially with regard to the magnetic arrangement 30 and the pole shoe arrangement 33. As also explained in greater detail below, the pole shoe arrangement 33 and the magnetic arrangement 30 are essentially more complex in design than in the exemplary embodiment according to FIG. 12.

Figure 14:
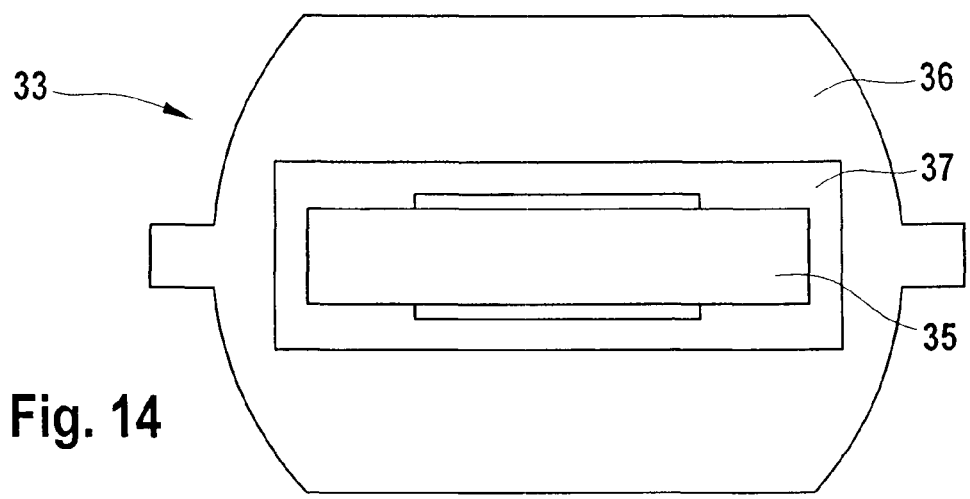
FIG. 14 is a top view of a pole shoe arrangement of the electric motor implementation from FIG. 12.

FIG. 14 shows the pole shoe arrangement 33 of the electric motor shown in FIG. 12, seen here in a view from above. The pole shoe arrangement 33 has an internal pole shoe element 35 and an external pole shoe element 36, which, together with the internal pole shoe element 35, is arranged in a plane and surrounds the internal pole shoe element 35 radially. The internal pole shoe element 35 is designed generally as a rectangle. The external pole shoe element 36 has a shape that is coordinated with the coil housing 29 and protrudes radially beyond the coil housing 29. In its internal area, the external pole shoe element 36 has a recess 37, the shape of which is coordinated with the internal pole shoe element 35 and accordingly has a rectangular cross section. The internal pole shoe element 35 is arranged in the recess 37. The internal pole shoe element 35 is attached to the coil core 28 in the installed state. The external pole shoe element 36 is attached to the coil housing 29 in the installed state. With clearance between the internal pole shoe element 35 and the external pole shoe element 36, the coil housing 29 is generally closed by the pole shoe arrangement 33.

Figure 15:
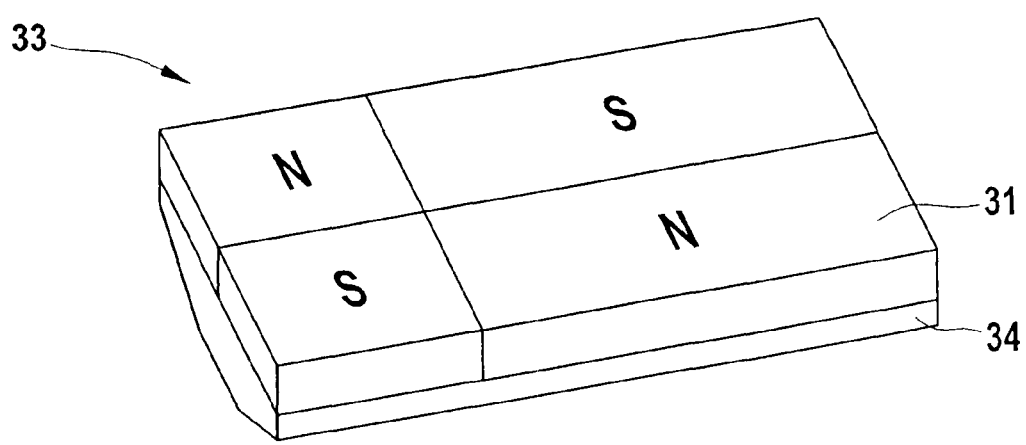
FIG. 15 is a perspective view of one magnetic arrangement in the electric motor implementation of FIG. 12.

FIG. 15 shows the magnetic arrangement 30 of the electric motor 1 of FIG. 12. The perspective here is selected so that the side of the magnetic arrangement 30 facing the pole shoe arrangement 33 in the installed state is visible. The magnetic arrangement 30 has two permanent magnets 31 arranged side by side on the carrier 34 with an antiparallel polarity. In parallel with their north/south extent, the permanent magnets 31 have the same dimensions. Across the north/south extent, the permanent magnet 31 shown at the right in FIG. 15 has dimensions that are twice as large as those of the permanent magnet 31 shown at the left in FIG. 15. The different dimensions of the permanent magnets 31 result in a force as well as a torque being exerted on the magnetic arrangement 30 in energization of the coil 27. In this way, as described in detail with reference to FIG. 11, a pendulum vibration and/or a bending vibration and rotational vibration of the magnetic arrangement 30 including the components associated therewith can be generated.

As an alternative to using multiple permanent magnets 31, a single permanent magnet 31 having differently magnetized regions can also be used. This also applies to magnetic arrangements 30 designed differently than those shown in FIG. 15.

Figure 16:
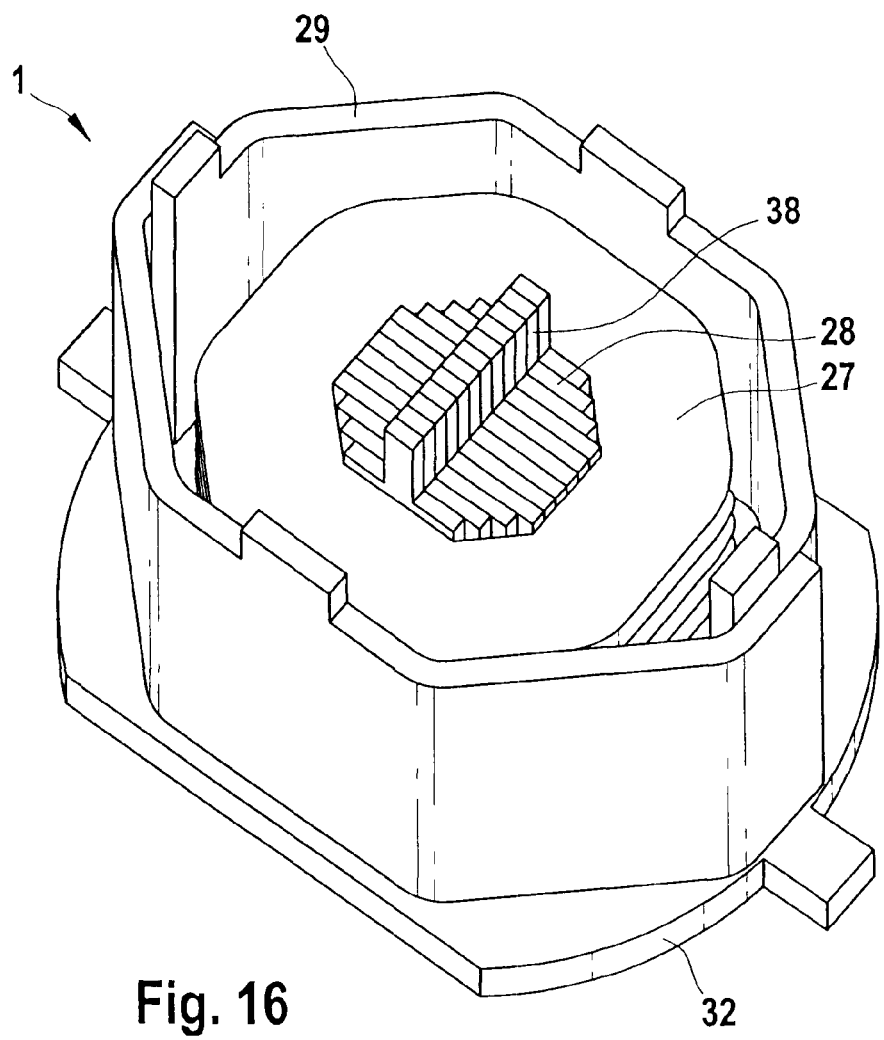
FIG. 16 is a perspective view of the electric motor of FIG. 13, without the magnetic arrangement and without the pole shoe arrangement.

FIG. 16 shows the electric motor 1 of FIG. 13 without the magnetic arrangement 30 and without the pole shoe arrangement 33. The coil core 28 is designed as an octagon and has an axial extension 38 on the axial end of the pole shoe arrangement 33, said extension 38 having a rectangular cross section. The coil 27 surrounds the coil core 28 with an approximately constant cross section. The coil housing 29 is also designed to have an octagonal cross section, so there is a small gap between the coil 27 and the coil housing 29, and the coil 27 together with the coil core 28 occupies the coil housing 29.

Figure 17:
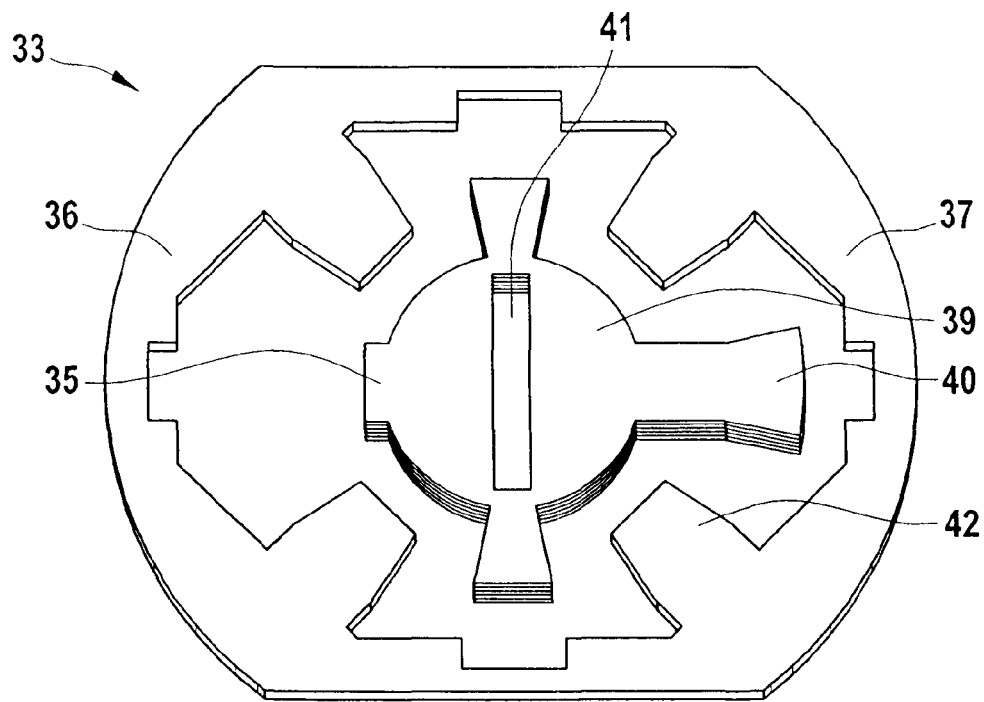
FIG. 17 is a perspective view of the pole shoe arrangement of the electric motor of FIG. 16.

FIG. 17 shows the pole shoe arrangement 33 of the electric motor 1 of FIG. 13. By analogy with FIG. 14, the pole shoe arrangement 33 in turn has an internal pole shoe element 35 and an external pole shoe element 36, surrounding the internal pole shoe element 35 radially. The internal pole shoe element 35 is arranged in the recess 37 of the external pole shoe element 36 and is embodied as a circular disk 39 having four radial extensions 40, all arranged in pairs opposite one another with different radial extents. In the area of the center of the circular disk 39, the internal pole shoe element 35 has a rectangular perforation 41, which is coordinated with the outside contour of the axial extension 38 on the coil core 28, so that the internal pole shoe element 35 can be pushed onto the axial extension 38 of the coil core 28. A similar type of fastening may be selected for the pole shoe arrangement 33 shown in FIG. 14.

The recess 37 in the external pole shoe element 36 is coordinated with the internal pole shoe element 35 and has two planes of symmetry perpendicular to one another, intersecting one another at the center of the recess 37. The external pole shoe element 36 here has four protrusions 42, which extend radially inward into the recess 37 and are rotated by 45° with respect to the radial extensions 40 of the internal pole shoe element 35.

Figure 18:
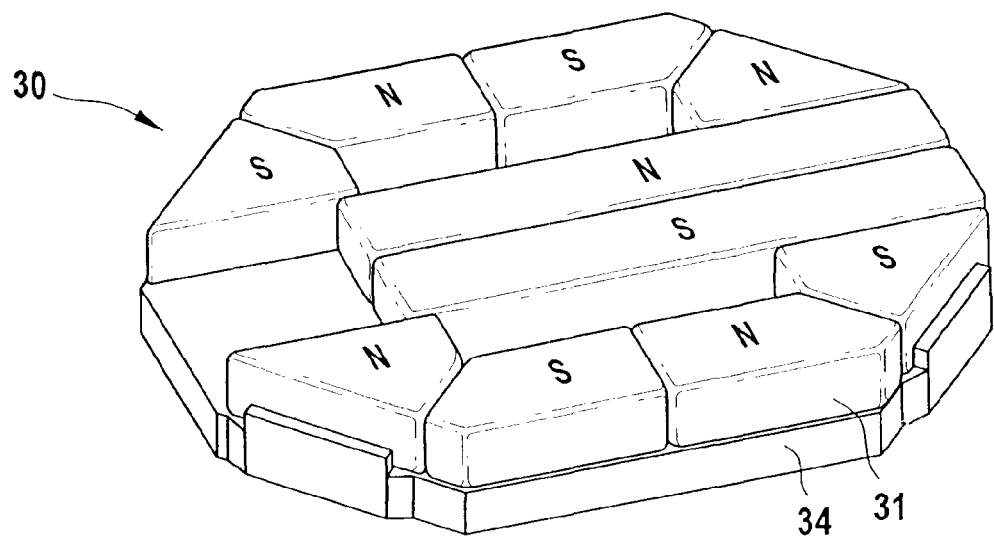
FIG. 18 is a perspective view of the magnetic arrangement of the electric motor of FIG. 16.

FIG. 18 shows the magnetic arrangement 30 of the electric motor 1 of FIG. 13. By analogy with FIG. 15, the magnetic arrangement 30 in FIG. 18 also has a plurality of permanent magnets 31 arranged on the carrier 34. The arrangement of permanent magnets 31 is in the form of two half-shells arranged opposite one another at a distance with opposite polarities, a rectangular-shaped permanent magnet 31 being arranged between them. By means of the pole shoe arrangement 33 shown in FIG. 17, a force and a torque can be exerted on the magnetic arrangement 30 illustrated in FIG. 18 when electric current flows through the coil 27. Through the configuration of the permanent magnets 31, it is possible to predetermine which partial areas of the magnetic arrangement 30 will serve to generate the force and which partial areas will serve to generate the torque.

The drive principle described above may also be used in electric toothbrushes or other personal care devices or tools of different designs.

A number of embodiments of the invention have been described. Nevertheless, it will be understood that various modifications may be made without departing from the spirit and scope of the invention. For example, any number of combinations of translational, rotational, osciallatory, or vibrational movements can be generated using magnetic fields, or combinations of magnetic fields and other mechanical actuator or drivers. Accordingly, other embodiments are within the scope of the following claims.

The invention claimed is:

1. An electric toothbrush drive device configured to drive a brush element, the drive device comprising:
   a first drive component configured to generate a magnetic field;

a second drive component configured to be driven to both translatory movement and rotational movement by the influence of the magnetic field; and a transmission element configured to be deflected out of a predefined position to transmit a translatory movement and a rotational movement of the second drive component to the brush element;

wherein deflection of the transmission element out of the predefined position varies along a longitudinal axis of the transmission element;

wherein the second drive component is arranged axially next to the first drive component; and wherein the magnetic field generated by the first drive component extends axially towards the second drive component to engage the second drive component.

2. The drive device according to claim 1, wherein the predefined position of the transmission element corresponds to an equilibrium position characterized by an absence of action of the magnetic field on the second drive component.

3. The drive device according to claim 2, wherein the equilibrium position is outside of a maximum working range of the transmission element.

4. The drive device according to claim 1, wherein the transmission element executes a primarily rotational movement in at least one position along its length in the transmission of the translatory movement and the rotational movement to the second drive component.

5. The drive device according to claim 1, wherein a component of the deflection of the transmission element oriented across the longitudinal axis of the transmission element varies linearly.

6. The drive device according to claim 1, wherein the deflection of the transmission element out of the predefined position comprises a first range in a first direction and a second range in a second direction opposite the first direction along a longitudinal axis of the transmission element.

7. The drive device according to claim 1, wherein the transmission element is excitable to a translatory vibration and to a rotational vibration.

8. The drive device according to claim 7, wherein the translatory vibration and the rotational vibration are of different resonant frequencies.

9. The drive device according to claim 7, wherein the transmission element can be excited to a pendulum vibration about a pendulum axis running across the longitudinal axis of the transmission element.

10. The drive device according to claim 7, wherein the transmission element can be excited to a bending vibration across the longitudinal axis of the transmission element.

11. The drive device according to claim 10, wherein the transmission element can be selectively excited to at least one of the pendulum vibration and the bending vibration.

12. The drive device according to claim 7, further comprising a suspension configured to support the transmission element and to allow at least one of rotational and translational vibration of the transmission element.

13. The drive device according to claim 12, comprising multiple suspensions configured to allow, separately, the rotational vibration and the translatory vibration of the transmission element.

14. The drive device according to claim 12, wherein the suspension is arranged in one of an area of the pendulum axis of the transmission element, an area of a vibration node of the transmission element, and an area of an axial end of the transmission element.

15. The drive device according to claim 12, wherein, at least one suspension comprises an elastic element.

16. The drive device according to claim 1, wherein the transmission element has a coupling area configured to couple the brush element and wherein a ratio of vibration amplitudes can be varied between the translatory vibration and the rotational vibration of the transmission element in the coupling area of the transmission element.

17. The drive device according to claim 16, wherein the coupling area predefines through its shape an orientation of the brush element relative to the transmission element, so that bristles arranged on the brush element form an acute angle with a deflection direction of the translatory vibration of the transmission element.

18. The drive device according to claim 1, wherein the transmission element is rigidly connected to the second drive component in a rotationally fixed manner.

19. The drive device according to claim 1, wherein the first drive component comprises a coil.

20. The drive device according to claim 1, wherein the first drive component comprises a pole shoe arrangement with an internal pole shoe element and an external pole shoe element radially surrounding the internal pole shoe element.

21. The drive device according to claim 1, wherein the second drive component comprises a permanent magnet.

22. The drive device according to claim 1, wherein the first drive component and the second drive component are arranged inside a housing comprising a ferromagnetic material.

23. A drive device for driving a brush element of an electric toothbrush, the drive device comprising:

a first drive component configured to generate a magnetic field;

a second drive component configured to be driven to both translatory and rotational movement by action of the magnetic field; and a transmission element configured to be deflected out of a predefined position to transmit a translatory movement and a rotational movement of the second drive component to the brush element along a longitudinal axis of the transmission element;

wherein the transmission element is attached to a suspension between two freely movable axial ends of the transmission element;

wherein the second drive component is arranged axially next to the first drive component; and wherein the magnetic field generated by the first drive component extends axially towards the second drive component to engage the second drive component.

24. The drive device according to claim 23, wherein the suspension comprises an elastic element.

25. The drive device according to claim 23, further comprising a rotatable plate spring arrangement configured to generate a rotational vibration.

26. A drive device for driving a brush element of an electric toothbrush, the drive device comprising:

a first drive component configured to generate a magnetic field; and a second drive component comprising a magnetic arrangement arranged axially next to the first drive component and comprising a plurality of magnetic regions, wherein the magnetic field generated by the first drive component extends axially towards the plurality of magnetic regions of the second drive component to engage said plurality of magnetic regions, and wherein the magnetic regions in the magnetic arrangement are arranged according to a pattern that is neither axially symmetrical nor point symmetrical.

27. The drive device according to claim 26, wherein the magnetic regions comprise at least one of permanent magnets and magnetizable regions of different sizes.

28. An electric toothbrush, comprising:
- a shaft configured to accept an attachable brush element thereon;
- a first drive component connected to the shaft and configured to generate a magnetic field; and
- a second drive component comprising a magnetic arrangement arranged axially next to the first drive component and comprising a plurality of magnetic regions comprising at least one of permanent magnets and magnetizable regions, wherein the magnetic field generated by the first drive component extends axially to the magnetic arrangement of the second drive component to engage said magnetic arrangement; and
- wherein the magnetic arrangement is designed with respect to the dimensions and the magnetic orientation of the magnetic regions so that when the magnetic field generated by the first drive component is in effect, a force and a torque are exerted on the second drive component to drive the shaft and the brush element of the electric toothbrush.

\* \* \* \* \*